United States Patent
Rusnak

(10) Patent No.: US 9,301,736 B2
(45) Date of Patent: Apr. 5, 2016

(54) FINE NEEDLE BIOPSY WITH ADAPTOR

(71) Applicant: Joseph G. Rusnak, East Aurora, NY (US)

(72) Inventor: Joseph G. Rusnak, East Aurora, NY (US)

( * ) Notice: Subject to any disclaimer, the term of this patent is extended or adjusted under 35 U.S.C. 154(b) by 392 days.

(21) Appl. No.: 14/032,370

(22) Filed: Sep. 20, 2013

(65) Prior Publication Data
US 2014/0018699 A1    Jan. 16, 2014

Related U.S. Application Data

(63) Continuation-in-part of application No. 12/432,792, filed on Apr. 30, 2009, now abandoned.

(51) Int. Cl.
| | | |
|---|---|---|
| *A61B 10/02* | (2006.01) | |
| *A61B 17/34* | (2006.01) | |
| *A61B 17/00* | (2006.01) | |

(52) U.S. Cl.
CPC .......... *A61B 10/0266* (2013.01); *A61B 10/0233* (2013.01); *A61B 10/0275* (2013.01); *A61B 10/0283* (2013.01); *A61B 17/3417* (2013.01); *A61B 2017/00486* (2013.01)

(58) Field of Classification Search
CPC ........... A61B 10/0233; A61B 10/0266; A61B 2017/00486
See application file for complete search history.

(56) References Cited

U.S. PATENT DOCUMENTS

| | | | |
|---|---|---|---|
| 3,630,192 A | 12/1971 | Jamshidi | |
| 4,099,518 A | 7/1978 | Baylis et al. | |
| 4,177,797 A | 12/1979 | Baylis et al. | |
| 5,005,585 A | 4/1991 | Mazza | |
| 5,487,725 A | 1/1996 | Peyman | |
| 6,863,676 B2 | 3/2005 | Lee et al. | |
| 6,908,440 B2 | 6/2005 | Fischer | |
| 7,331,930 B2 | 2/2008 | Faciszewski | |
| 7,384,400 B2 | 6/2008 | Goldenberg | |
| 8,384,537 B1 | 2/2013 | Simmons | |
| 2001/0009978 A1 | 7/2001 | Krueger et al. | |
| 2004/0073139 A1 | 4/2004 | Hirsch et al. | |
| 2005/0177117 A1 | 8/2005 | Crocker et al. | |
| 2007/0219459 A1 | 9/2007 | Cohen | |
| 2008/0045860 A1 | 2/2008 | Miller et al. | |

FOREIGN PATENT DOCUMENTS

GB        2290030 A   *   12/1995  ............ A61M 25/06

OTHER PUBLICATIONS

Kim et al., "US-Guided Fine-Needle Aspiration of Thyroid Nodules: Indications, Techniques, Results," RadioGraphics, vol. 28, pp. 1869-1889 (Nov.-Dec. 2008).

* cited by examiner

*Primary Examiner* — Lee S Cohen
*Assistant Examiner* — Emily Lloyd
(74) *Attorney, Agent, or Firm* — Bond Schoeneck & King

(57) ABSTRACT

Disclosed herein is a biopsy needle system, an adaptor for the system, and a method of using the system. The system includes an outer needle, an inner needle, and an adaptor. The outer needle has a longitudinal passage, a length, and a hub on the proximal end of the outer needle. The inner needle has a longitudinal passage and a length that is greater than the length of the outer needle. The inner needle is configured to fit within the longitudinal passage of the outer needle. The adaptor is configured to fit within the hub of the outer needle and includes a tapered longitudinal passage that guides a distal end of the inner needle through the adaptor and into the longitudinal passage of the outer needle.

4 Claims, 13 Drawing Sheets

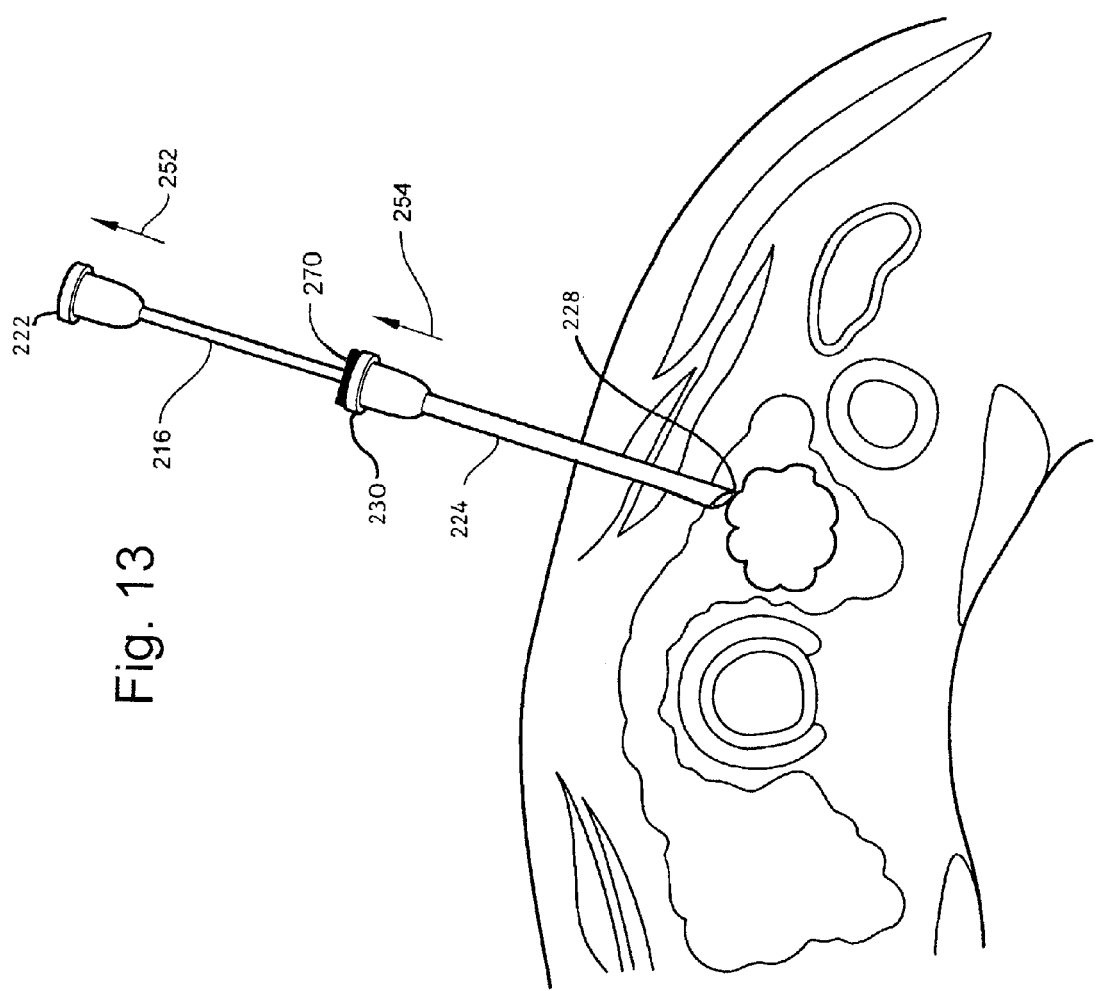

FINE NEEDLE BIOPSY WITH ADAPTOR

RELATED APPLICATION

This application is a continuation-in-part of U.S. application Ser. No. 12/432,792, filed Apr. 30, 2009, now abandoned. The entire teachings of the above application are incorporated herein by reference.

BACKGROUND OF THE INVENTION

The development of non-invasive assays for diagnosing certain types of cancer has provided practitioners with some options for diagnosis of cancer and other related disease without the need for tissue biopsy. However, such options are limited in their applications and effectiveness. The most definitive test for cancer or related disease is still tissue biopsy. Tissue biopsy occurs when a sample of tissue from a site that is believed to be diseased is harvested and analyzed by a pathologist to determine the nature of the tissue and whether it is healthy tissue, benign tissue growth, or cancerous tissue. Tissue samples from small organs or glands, like lymph nodes or thyroid glands, are especially difficult to harvest due to the relatively small size of the organs or glands (and their respective growths or nodules), location in sites that are uncovered by everyday clothing, and proximity to significant blood vessels. Furthermore, vascularization in many glands or organs is considerable, making the possibility of bleeding a significant issue.

Processes for harvesting a tissue sample from a patient includes three types of procedures. First, open surgery occurs when a patient is cut open to expose the tissue from which a sample is required. The procedure is invasive and creates a considerable risk of infection and side effects as compared to less-invasive procedures. Of the three procedures for biopsy, it is generally considered the least desirable. The second procedure uses a core tissue biopsy needle. A core tissue biopsy needle requires removal of a relatively large piece of tissue from the desired tissue site. The tissue sample is large enough that it requires further processing, including slicing of the tissue sample to analyze under a microscope. An example of a core biopsy device is disclosed in U.S. Pat. No. 4,177, 797. The apparatus comprises an improved rotary biopsy device for extracting biopsy samples and the like from specific specimen extracting sites. The '797 patent indicated, in 1977, that a problem in the biopsy field was that prior biopsy devices had not been successful in providing high quality extracted specimens while at the same time minimizing trauma to the patient and providing easy removability of the specimen from the patient. U.S. Pat. No. 5,005,585 discloses a core biopsy needle construction that has an elongated needle member with a sharp annular interior edge. At the time of its filing, the '585 patent commented on the state of the art as follows, "In the past, biopsy procedures have been carried out using a hollow needle of varying internal diameter with a tapered distal end and a diagonal cutting edge . . . . Although biopsy needles of this construction have met with success, failure to obtain an adequate core biopsy specimen frequently occurs. Not infrequently, biopsy specimens will be left behind . . . thus necessitating the need for attempting another pass at obtaining a core biopsy."

Another technique for harvesting tissue is fine needle aspiration (FNA). Fine needle aspiration removes smaller samples of biopsy tissue that can typically be viewed under a microscope without tissue slicing. The FNA procedure is as follows. A patient is given a local anesthetic. A needle (typically a 20-30 gauge needle) is inserted hypodermically and positioned to the site of the targeted tissue. The needle often penetrates fat tissue and muscular tissue depending on the location of the targeted tissue. The organ or gland is held stationary relative to the movement of the needle. Then, the needle is gently moved into the tissue, thereby causing the needle to take a thin sample of the tissue. The tissue is drawn into the needle either by aspiration or by the capillary action of the needle. Aspiration occurs with the use of a vacuum source such as a syringe. To aid in harvesting an adequate sample size, the needle is optionally moved in and out of the puncture site from about one to five times. This reciprocating motion causes cellular material to be scraped from the tissue and drawn into the needle. Then, the needle is withdrawn from the patient and the tissue collected in the needle is placed on a slide for pathological analysis. Since the individual tissue specimens are smaller/thinner than a core biopsy, no additional tissue slicing is required. The sample can be placed on a slide, stained, and analyzed. Often, with current FNA needles, the process is repeated to obtain between eight and eighteen slides with tissue samples.

U.S. Pat. No. 6,908,440 discloses a fine needle aspiration system with a first sharp edge at the beveled distal end of the needle that scrapes tissue during proximal to distal travel of the needle. The '440 patent discusses a drawback of fine needle aspiration: "[T]he FNA [fine needle aspiration] biopsy needle procedure fails to collect a sample of sufficient size to enable definitive pathological results. When this happens, the physician must repeat the procedure causing additional trauma to the body part undergoing biopsy and creating additional risk of an adverse event." Additionally, Kim et al., "US-guided Fine-Needle Aspiration of Thyroid Nodules: Indications, Techniques, Results," RadioGraphics, Volume 28, Number 7, pp. 1869-1899 (November 2008), is a review of current FNA results using ultrasound (US) versus palpation techniques. Despite many proposed designs for biopsy needles, standard hypodermic needles having a size of between 20 and 30 gauge are still the industry standard. Kim concludes, "[h]owever, the achievement of optimal results of the thyroid FNA, with increased efficacy and decreased inadequacy results, requires not only a skillful aspiration technique and attention to the factors that affect material adequacy but also awareness of the indications for and limitations of FNA biopsy . . . . US-guided FNA yields an inadequate specimen in 10%-20% of procedures . . . . "

SUMMARY OF THE INVENTION

After many years of others attempting to develop a biopsy needle system that is an improvement over the standard FNA methods and that can efficiently obtain adequate FNA quality samples while minimizing variation in biopsy procedure success caused by the level of practitioner experience, the systems, apparatuses, and methods disclosed herein have been developed to address these and other concerns.

One embodiment of the present invention is a biopsy needle system including an outer needle, an inner needle, and an adaptor. The outer needle has a longitudinal passage, a length, and a hub on the proximal end of the outer needle. The inner needle has a longitudinal passage and a length that is greater than the length of the outer needle. The inner needle is configured to fit within the longitudinal passage of the outer needle. The adaptor is configured to fit within the hub of the outer needle and includes a tapered longitudinal passage that guides a distal end of the inner needle through the adaptor and into the longitudinal passage of the outer needle.

In many embodiments, the tapered longitudinal passage of the adaptor is an elongated funnel shape. In some embodiments, the adaptor may include a plastic core containing the tapered longitudinal passage, and an outer elastomeric layer to create a tight fit within the hub of the outer needle. The hub of the outer needle may be a male luer fitting, and the adaptor can include a female luer fitting to attach to the male luer fitting of the outer needle. As an example of some suitable needle gauges, the inner needle may be a 25-gauge needle, in which case the outer needle can be a 19- or 20-gauge needle. As an example of some suitable needle lengths, the outer needle can be one inch in length and the inner needle can be 2.5 inches in length.

Another example embodiment of the present invention is an adaptor for a biopsy needle system having an outer needle and an inner needle configured to fit within a longitudinal passage of the outer needle. The adaptor includes a cylindrical body configured to fit within a hub of the outer needle. The cylindrical body includes a tapered longitudinal passage that guides a distal end of the inner needle through the cylindrical body and into the longitudinal passage of the outer needle. In many embodiments, the tapered longitudinal passage of the cylindrical body is an elongated funnel shape. In some embodiments, the cylindrical body may include a plastic core containing the tapered longitudinal passage, and an outer elastomeric layer to create a tight fit within the hub of the outer needle. The hub of the outer needle may be a male luer fitting, and the cylindrical body can include a female luer fitting to attach to the male luer fitting of the outer needle.

Another example embodiment of the present invention is a method of sampling tissue. The method involves inserting an adaptor having a cylindrical body into a hub of an outer needle, inserting the outer needle into a patient, and positioning the outer needle adjacent a site of tissue sampling. A distal end of an inner needle is then inserted through a tapered longitudinal passage of the adaptor and into a longitudinal passage of the outer needle. The inner needle is extended through the longitudinal passage of the outer needle to position the distal end of the first inner needle adjacent the site of tissue sampling. The inner needle is then moved in a reciprocating motion within the outer needle to cause the distal end of the first inner needle to aspirate tissue from the site of tissue sampling into a longitudinal passage of the first inner needle. The inner needle is then removed from the site of tissue sampling and outer needle, and a distal end of a second inner needle is inserted though the tapered longitudinal passage of the adaptor and into the longitudinal passage of the outer needle. Similar to the first inner needle, the second inner needle is extended through the longitudinal passage of the outer needle to position the distal end of the second inner needle adjacent the site of tissue sampling, and is moved in a reciprocating motion within the outer needle to cause the distal end of the second inner needle to aspirate additional tissue from the site of tissue sampling into a longitudinal passage of the second inner needle. In some embodiments, the site of tissue sampling is a thyroid gland, lymph node, or other soft tissue.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIGS. 10-13 illustrate example steps for sampling tissue, according to an example embodiment of the present invention.

DETAILED DESCRIPTION OF THE INVENTION

A description of example embodiments of the invention follows.

Disclosed herein is a fine needle biopsy system that has improved delivery to the site of tissue biopsy. The biopsy system uses an outer needle to deliver an inner needle to the tissue biopsy site. The system is designed to more efficiently harvest or sample tissue and is capable of being positioned with minimal pain, tissue trauma, and bleeding. The harvesting of the tissue is capable of adequate sample size without unnecessary tissue damage.

The needle biopsy system uses two standard hypodermic needles to perform a biopsy or aspirate; that is, using currently available needles, one as an outer needle (e.g., 19- or 20-gauge needle), which can also be referred to as a trocar, and the other as an inner needle (e.g., 25-gauge needle), which can also be referred to as an aspirate or biopsy needle. One problem with using standard hypodermic needles is that it is difficult to place a 25-gauge needle, for example, through a 19- or 20-gauge needle. The hub of the standard 19- or 20-gauge needle is not conducive for passing through another needle (e.g., a 25-gauge needle). That is because the opening of the longitudinal passage of the outer needle is very small compared to the opening of the hub of the outer needle. Attempting to insert the inner needle into the outer needle when the outer needle has already been inserted into a patent is dangerous for the patient and could cause much tissue trauma and bleeding. This is especially important with small soft tissue aspirates or biopsies, like thyroid tissue, where multiple biopsy needle passes may need to be used to get enough tissue for an adequate biopsy or aspirate sample. The disclosed adaptor can be inserted into the hub of the outer needle (trocar needle) and used to safely guide an inner needle (biopsy/aspirate needle) into the outer needle.

There are many advantages associated with the disclosed needle biopsy system. First, the clinical advantages of the system are that obtaining biopsies are quicker, less painful, and less traumatic to the surrounding tissue, and the samples obtained are of better quality. Inserting and removing the outer needle just once (though epidermis, muscle, and thyroid or other small tissue) allows for less damage to those tissues as well as cleaner samples to be obtained by the inner needle(s). The financial advantage of the system is its relatively low cost as standard needles can be obtained and the adaptor can be made relatively inexpensively.

Figure 1:
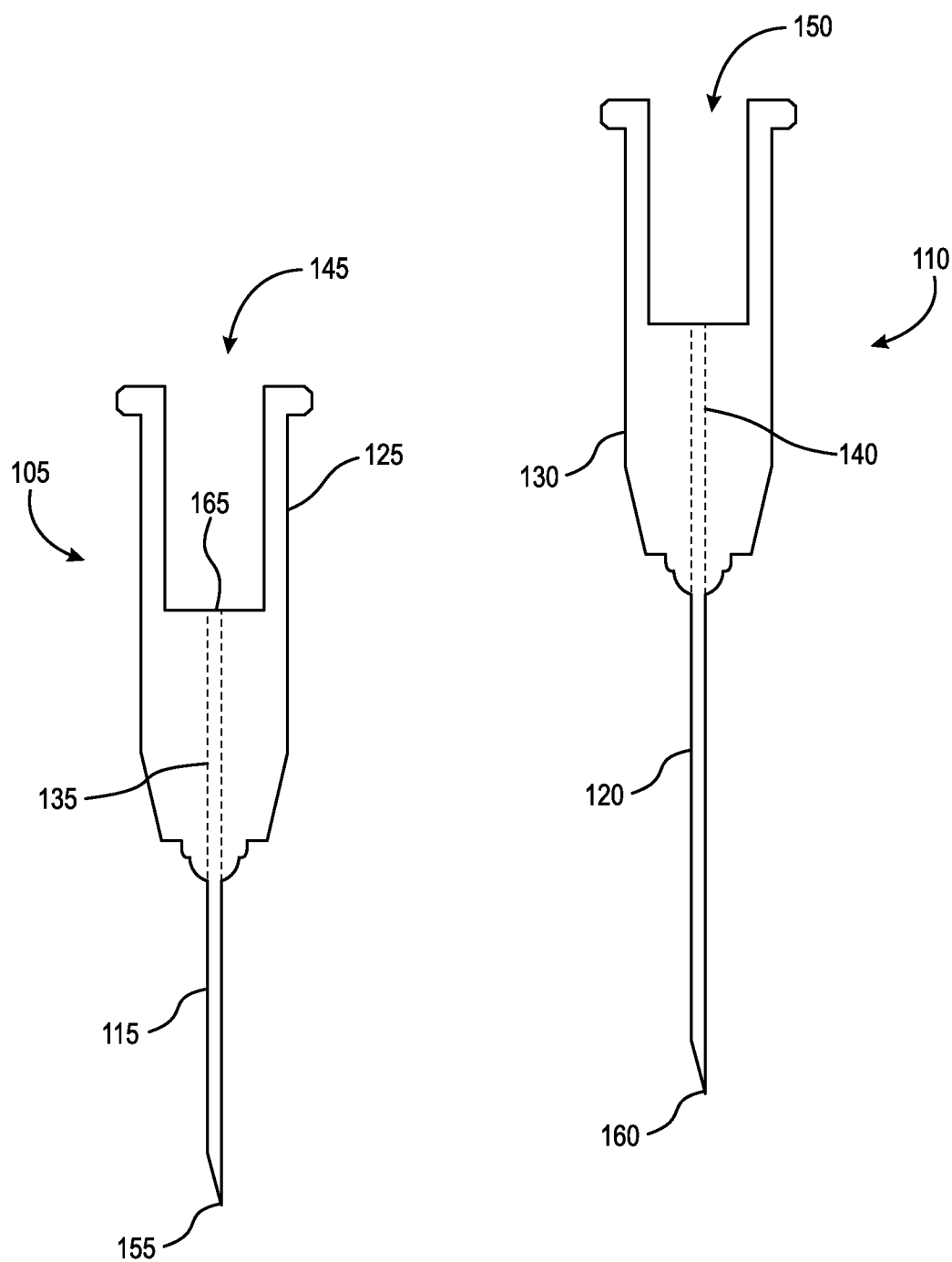
FIG. 1 illustrates standard hypodermic needles that can be used with the disclosed biopsy needle system.

FIG. 1 illustrates standard hypodermic needles 105, 110 that can be used with the disclosed biopsy needle system. The needles each have a shaft 115, 120, hub 125, 130, longitudinal passage 135, 140 through the shaft 115, 120 and hub 125, 130, opening in the hub 145, 150, and distal end 155, 160. Examples of suitable needles that may be used with the disclosed system are: for the outer needle 105, a one inch long, 19- or 20-gauge hypodermic needle; and for the inner needle 110, a 2.5 inch long, 25-gauge hypodermic needle. It should be understood by one skilled in the art that other size needles may be used, so long as the inner needle can fit within the outer needle, and that the inner needle is longer than the outer needle.

Figure 2:
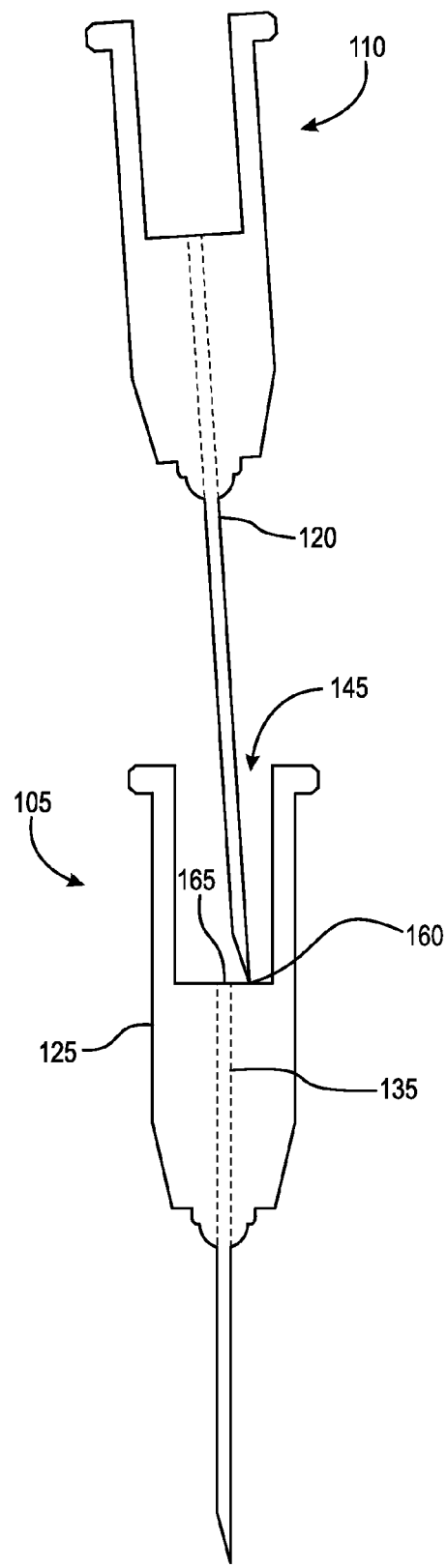
FIG. 2 illustrates problems associated with standard hypodermic needles being used as components of a biopsy needle system.

FIG. 2 illustrates problems associated with standard hypodermic needles 105, 110 being used as components of a biopsy needle system. As shown, it is difficult to place a 25-gauge needle 110, for example, through a 19- or 20-gauge needle 105. The hub 125 of the standard 19- or 20-gauge needle 105 is not conducive for passing through another needle (e.g., a 25-gauge needle) 110. That is because the opening 165 of the longitudinal passage 135 of the outer needle 105 is very small compared to the opening 145 of the hub 125 of the outer needle 105, and the distal end 160 of the inner needle 110 can get caught within the hub 125 of the outer needle 105. As mentioned above, attempting to insert the inner needle 110 into the outer needle 105 when the outer needle 105 has already been inserted into a patent is dangerous for the patient and could cause much tissue trauma and bleeding.

Figure 3:
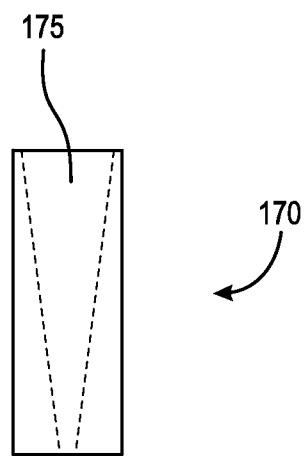
FIG. 3 illustrates an adaptor, according to an example embodiment of the present invention, that solves problems associated with standard hypodermic needles being used as components of a biopsy needle system.

FIG. 3 illustrates an adaptor 170, according to an example embodiment of the present invention, that solves problems associated with standard hypodermic needles 105, 110 being used as components of a biopsy needle system. The adaptor 170 includes a cylindrical body configured to fit within a hub 125 (FIG. 1) of the outer needle 105 (FIG. 1). The cylindrical body includes a tapered longitudinal passage 175 that guides a distal end 160 (FIG. 1) of the inner needle (FIG. 110) through the cylindrical body and into the longitudinal passage 135 (FIG. 1) of the outer needle 105 (FIG. 1). In the embodiment shown in FIG. 3, the tapered longitudinal passage 175 of the cylindrical body is an elongated funnel shape.

Figure 4:
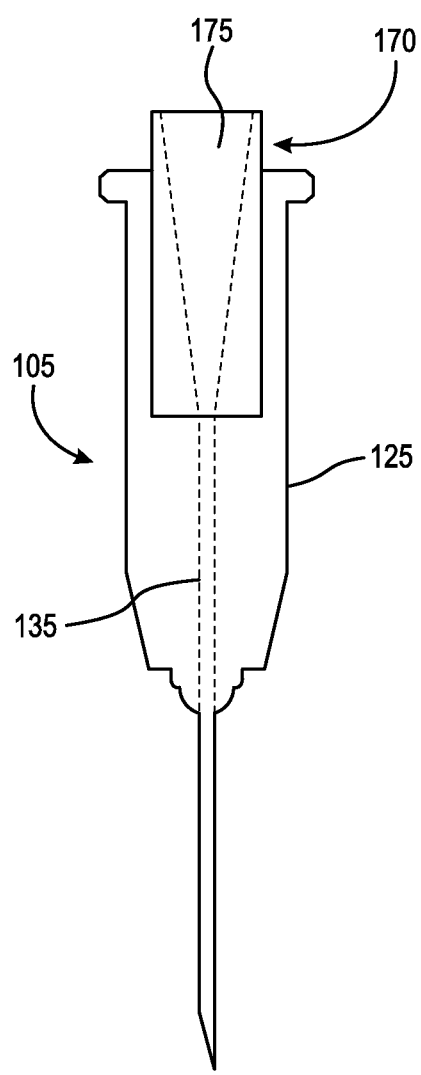
FIG. 4 illustrates an adaptor coupled to a standard hypodermic needle, according to an example embodiment of the present invention.

FIG. 4 illustrates the adaptor 170 coupled to a standard hypodermic needle 150, according to an example embodiment of the present invention. The adaptor 170 is inserted into the hub 125 of an outer needle 105. The lower end of the tapered longitudinal passage 175 matches with the opening of the longitudinal passage 135 of the outer needle 105. The adaptor 170 may fit snuggly into the hub 125 of the outer needle 105 due to its size or due to inclusion of a layer of elastomeric material around the outside of the adaptor 170.

Figure 5:
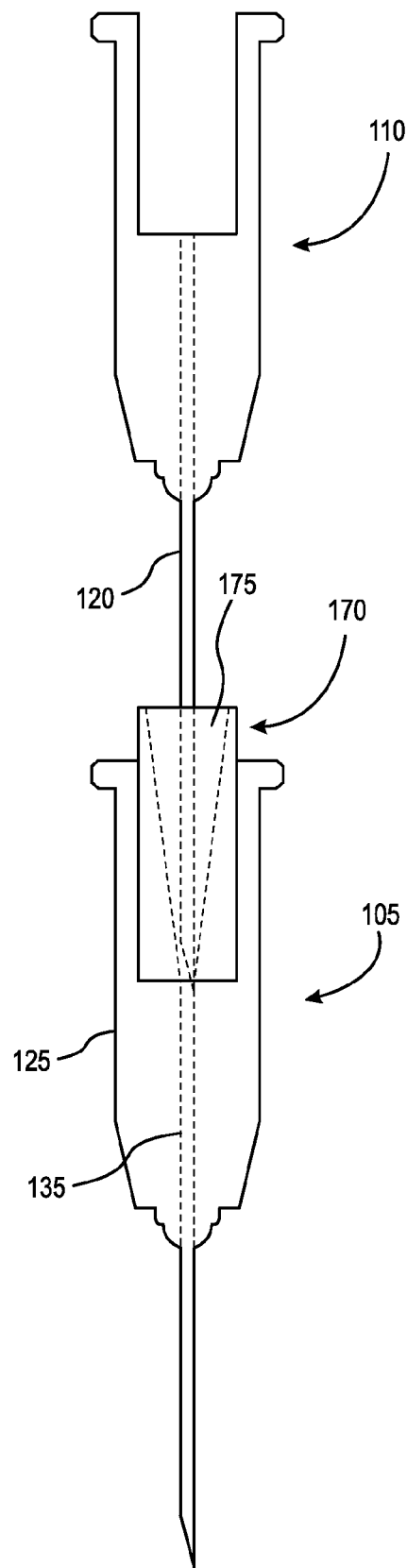
FIG. 5 illustrates an adaptor coupled to a standard hypodermic needle and a higher-gauge needle being inserted into the adaptor and first hypodermic needle, according to an example embodiment of the present invention.

FIG. 5 illustrates an adaptor 170 coupled to a standard hypodermic needle 105 and a higher-gauge needle 110 being inserted into the adaptor 170 and first hypodermic needle 105, according to an example embodiment of the present invention. When the adaptor 170 is inserted into the hub 125 of the outer needle 105, and the lower end of the tapered longitudinal passage 175 matches with the opening of the longitudinal passage 135 of the outer needle 105, a higher-gauge needle 110 can be inserted through the tapered longitudinal passage 175 of the adaptor 170 and into the longitudinal passage 135 of the outer needle 105 without getting caught within the hub 125 of the outer needle 105.

Figure 6:
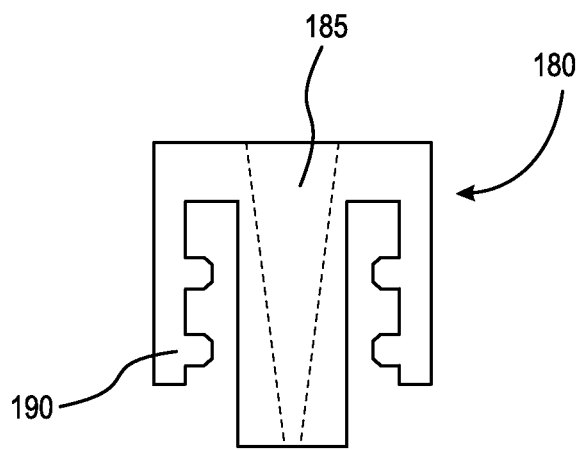
FIG. 6 illustrates an adaptor with a luer fitting, according to an example embodiment of the present invention.

FIG. 6 illustrates an adaptor 180 with a luer fitting 190, according to an example embodiment of the present invention. The adaptor 180 includes a cylindrical body configured to fit within a hub 125 (FIG. 1) of the outer needle 105 (FIG. 1). The cylindrical body includes a tapered longitudinal passage 185 that guides a distal end 160 (FIG. 1) of the inner needle (FIG. 110) through the cylindrical body and into the longitudinal passage 135 (FIG. 1) of the outer needle 105 (FIG. 1). In the embodiment shown in FIG. 6, the tapered longitudinal passage 185 of the cylindrical body is an elongated funnel shape. The adaptor 180 also includes a female luer fitting 190 configured to attach to a male luer fitting of an outer needle. It should be understood by one skilled in the art that the adaptor 180 can alternatively include a male luer fitting configured to attach to a female luer fitting of an outer needle.

Figure 7:
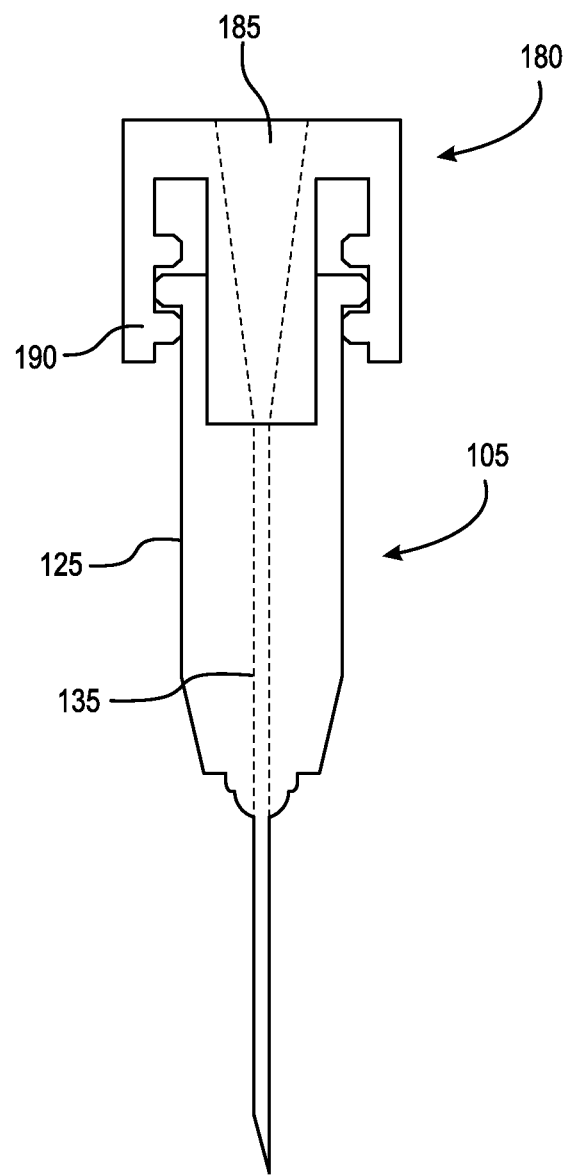
FIG. 7 illustrates an adaptor, with a luer fitting, coupled to a standard hypodermic needle, according to an example embodiment of the present invention.

FIG. 7 illustrates an adaptor 180, with a luer fitting 190, coupled to a standard hypodermic needle 105, according to an example embodiment of the present invention. The adaptor 180 is inserted into the hub 125 of an outer needle 105. The lower end of the tapered longitudinal passage 185 matches with the opening of the longitudinal passage 135 of the outer needle 105. The adaptor 180 may fit snuggly into the hub 125 of the outer needle 105 due to its size or due to inclusion of a layer of elastomeric material around the outside of the adaptor 180.

Figure 8:
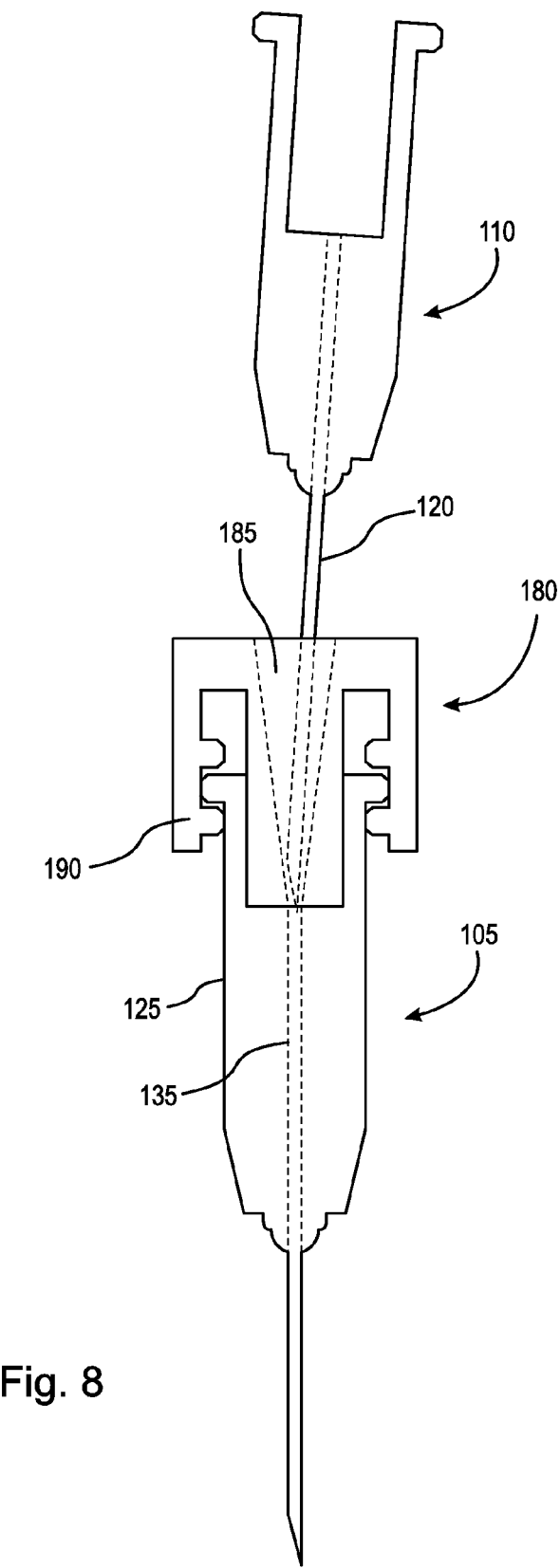
FIG. 8 illustrates an adaptor, with a luer fitting, coupled to a standard hypodermic needle and a higher-gauge needle being inserted into the adaptor and first hypodermic needle, according to an example embodiment of the present invention.

FIG. 8 illustrates an adaptor 180, with a luer fitting 190, coupled to a standard hypodermic needle 105 and a higher-gauge needle 110 being inserted into the adaptor 180 and first hypodermic needle 105, according to an example embodiment of the present invention. When the adaptor 180 is inserted into the hub 125 of the outer needle 105, and the lower end of the tapered longitudinal passage 185 matches with the opening of the longitudinal passage 135 of the outer needle 105, a higher-gauge needle 110 can be inserted through the tapered longitudinal passage 185 of the adaptor 180 and into the longitudinal passage 135 of the outer needle 105 without getting caught within the hub 125 of the outer needle 105.

Figure 9:
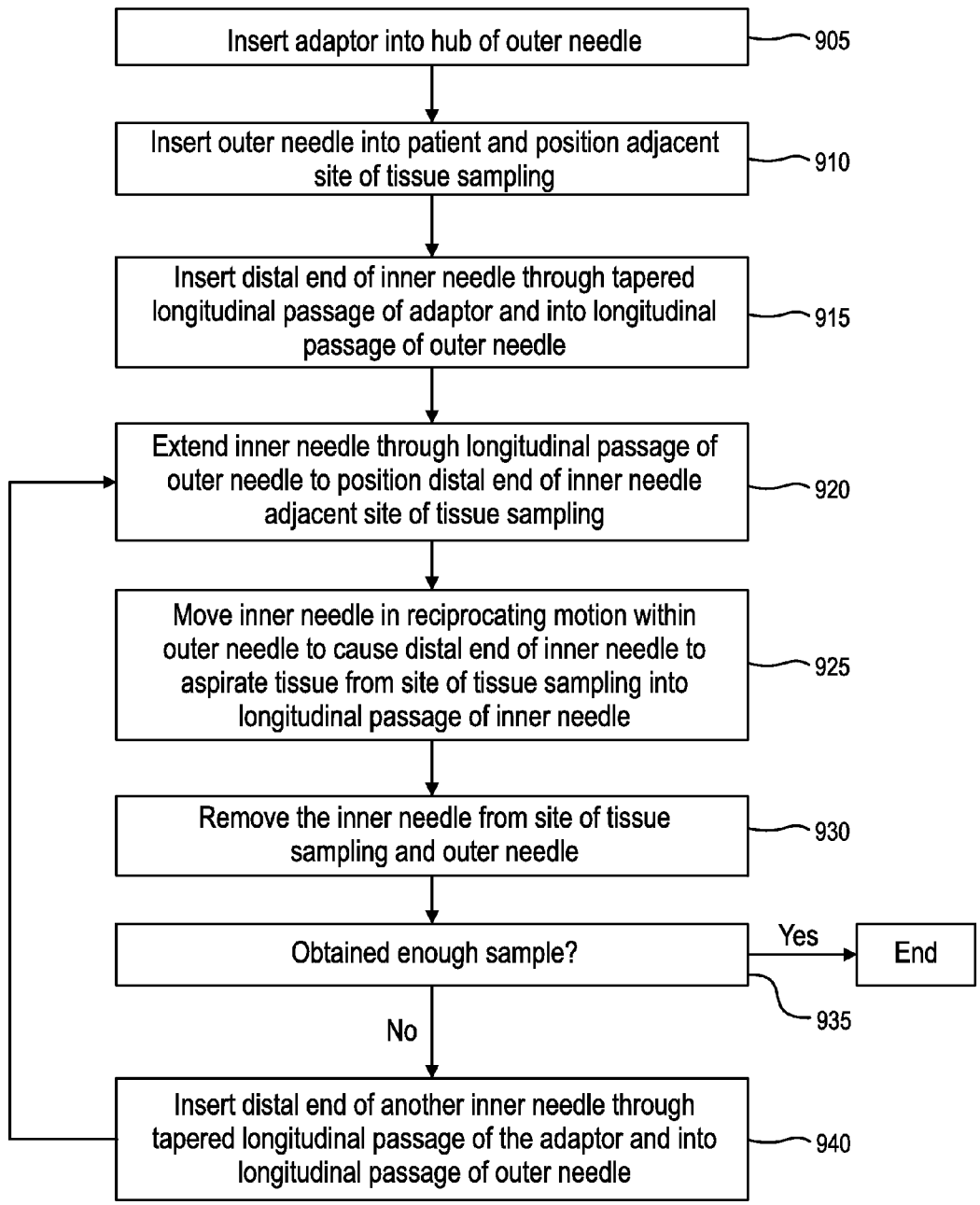
FIG. 9 illustrates a method of sampling tissue, according to an example embodiment of the present invention.

FIG. 9 illustrates a method of sampling tissue, according to an example embodiment of the present invention. The method involves inserting 905 an adaptor having a cylindrical body into a hub of an outer needle, inserting 910 the outer needle into a patient, and positioning 910 the outer needle adjacent a site of tissue sampling. A distal end of an inner needle is then inserted 915 through a tapered longitudinal passage of the adaptor and into a longitudinal passage of the outer needle. The inner needle is extended 920 through the longitudinal passage of the outer needle to position the distal end of the first inner needle adjacent the site of tissue sampling. The inner needle is then moved 925 in a reciprocating motion within the outer needle to cause the distal end of the first inner needle to aspirate tissue from the site of tissue sampling into a longitudinal passage of the first inner needle. The inner needle is then removed 930 from the site of tissue sampling and outer needle. If enough sample has been obtained 935, the method can end at this point. If additional sample is needed, a distal end of a second inner needle is inserted 940 though the tapered longitudinal passage of the adaptor and into the longitudinal passage of the outer needle. Similar to the first inner needle, the second inner needle is extended 920 through the longitudinal passage of the outer needle to position the distal end of the second inner needle adjacent the site of tissue sampling, and is moved 925 in a reciprocating motion within the outer needle to cause the distal end of the second inner needle to aspirate additional tissue from the site of tissue sampling into a longitudinal passage of the second inner needle. This process 920-940 can repeat until enough sample has been obtained.

FIGS. 10-13 illustrate example steps for sampling tissue, according to an example embodiment of the present invention. Although the illustration involves a tissue biopsy on a thyroid nodule, it should be understood by one skilled in the art that any desired tissue sample site could also be targeted.

Figure 10:
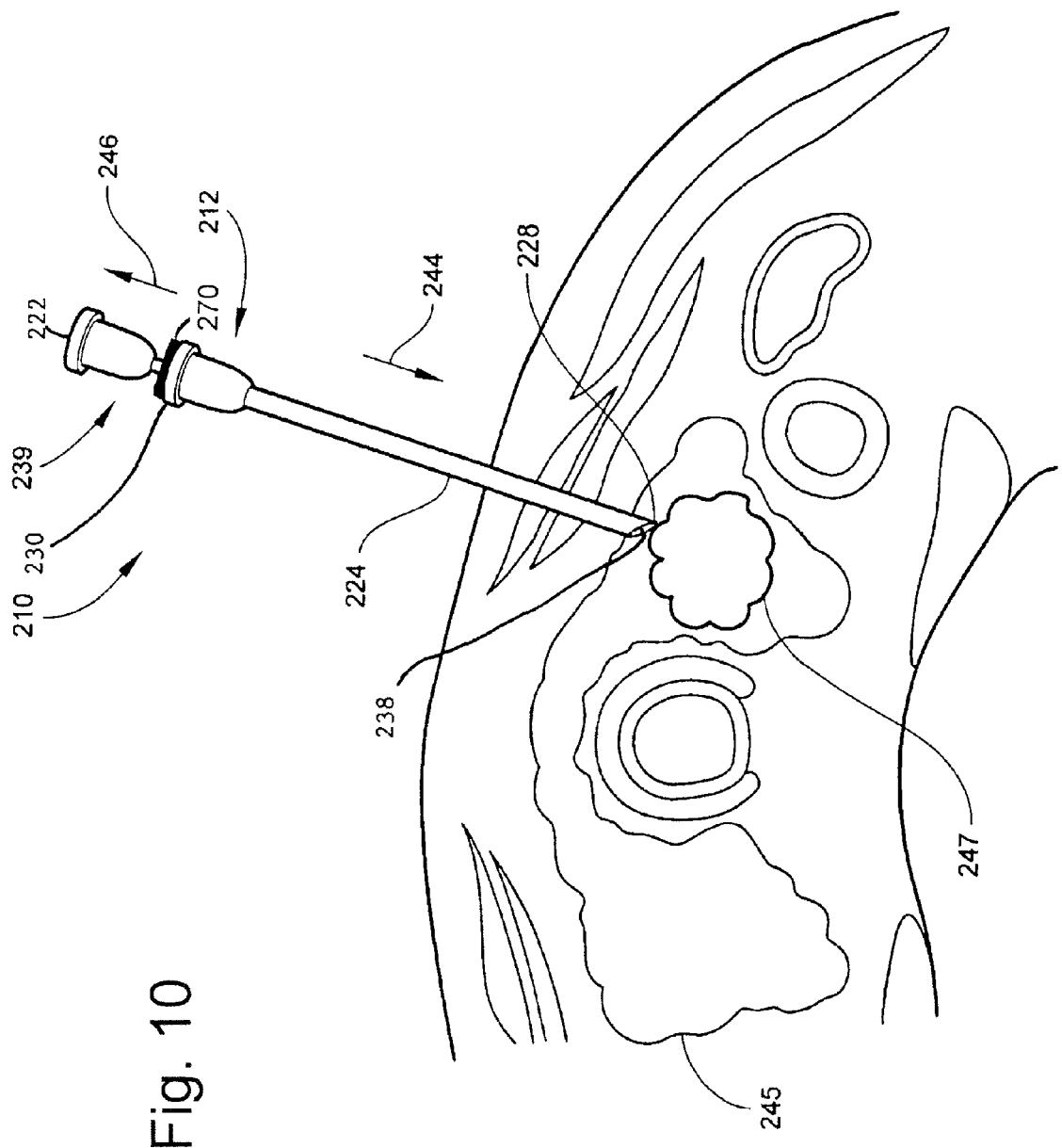

FIG. 10 shows deployment of the tissue biopsy system 210 including an outer needle 212, an adaptor 270, and an inner needle 239 within a longitudinal passage (not shown) of the outer needle. The outer needle 212 penetrates a patient hypodermically in the direction of arrow 244. The outer needle 212 has a slanted tip 228, defining a cutting edge that allows deployment with minimal tissue damage and as small an entry wound as possible. Once the outer needle 212 is positioned adjacent to the site of tissue harvesting, the inner needle 239 in extended beyond the tip 228 of the outer needle 212. The inner needle 239 is then removed in the direction of arrow 246. In one particular embodiment, the outer needle 212 is pushed into the tissue harvest site and withdrawn to create a passage into which the inner needle 239 later penetrates.

Figure 11:
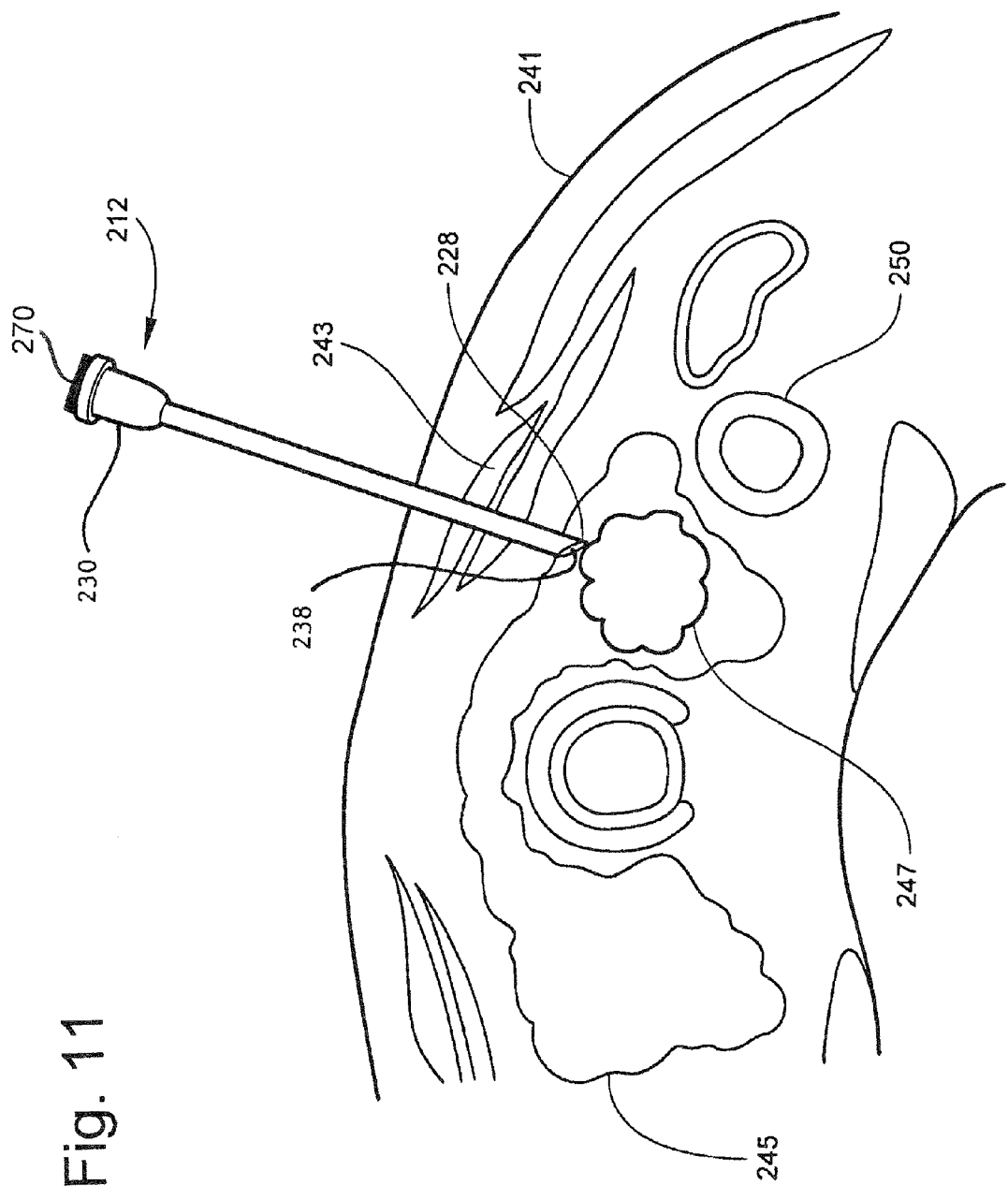

With reference to FIG. 11, the outer needle 212 is in the deployed position showing that it has passed through the patient's epidermis 241, muscular tissue 243, and tissue of a thyroid gland 245 either adjacent to or within a nodule 247. Avoidance of major blood vessels such as the carotid artery 250 is an important part of successful deployment of the biopsy system. In one embodiment, ultrasound visualization may assist in the safe deployment of the outer needle 212. The outer needle 212 also has inserted into its hub 230 an adaptor 270, like the adaptor disclosed with reference to FIG. 3.

Figure 12:
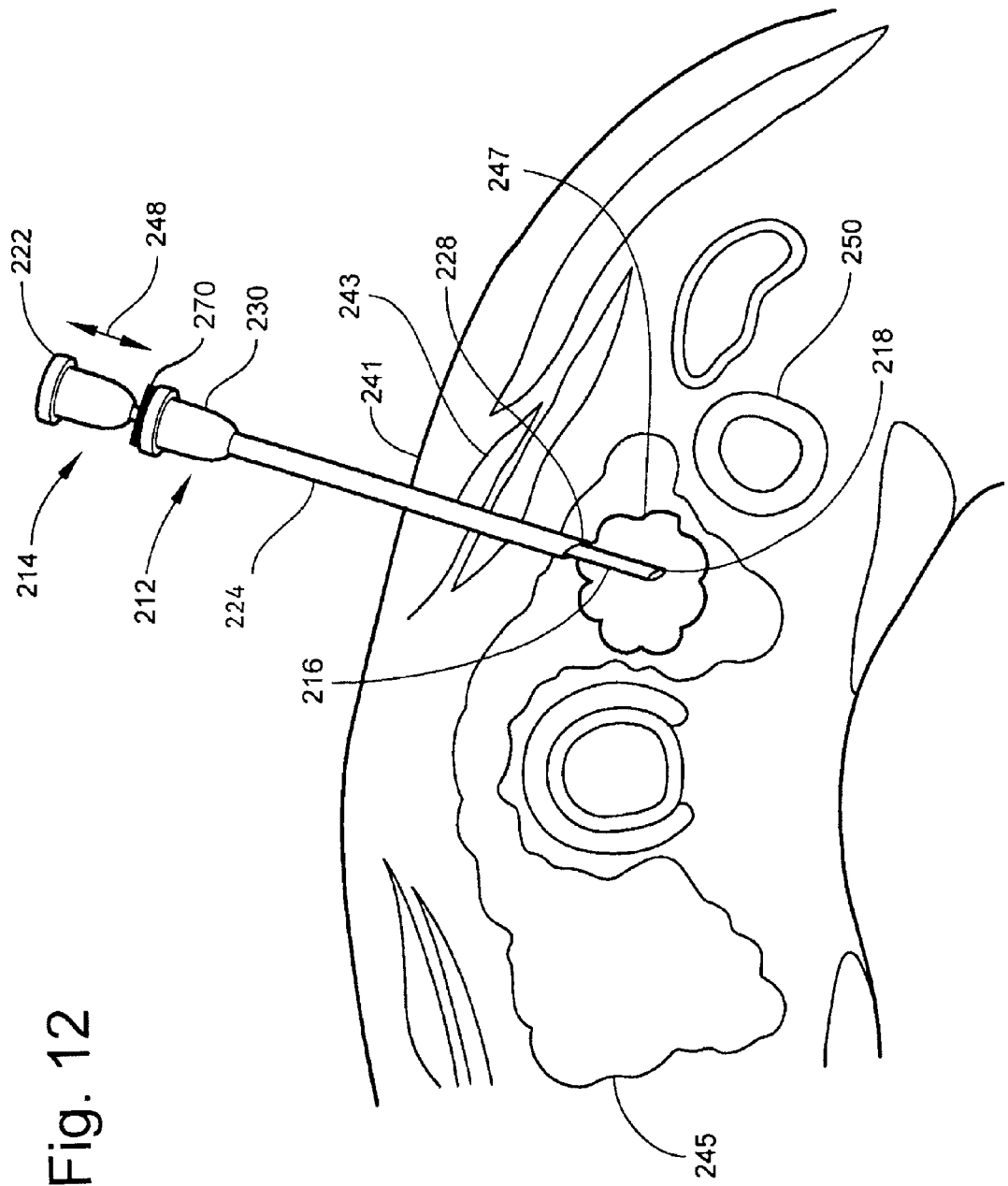

With reference to FIG. 12, an inner needle 214 is inserted through the adaptor 270 and into the longitudinal passage (not shown) of the outer needle 212. The operator grips the hub (e.g., luer fitting) 222 of the inner needle 214 and the hub 230 of the outer needle 212 and then pushes the inner needle 214 into the outer needle 212. As the distal end 218 of the inner needle 214 is pushed past the tip 228 of the outer needle 212, tissue harvesting begins as the cutting edge of the inner needle cuts or shaves tissue into its longitudinal passage (not shown). The tissue can be drawn in through aspiration or capillary forces of the inner needle 214. Although not shown, it is well within the scope of the present invention to have a hypodermic syringe affixed to the hub (e.g., luer fitting) 222 of the inner needle 214. As needed, the inner needle 214 can be repeatedly inserted and withdrawn into the tissue site as illustrated by direction arrow 248.

With reference to FIG. 13, after tissue harvesting is completed, the inner needle shaft 216 is withdrawn in the direction of arrow 252. The outer needle shaft 224 is likewise withdrawn in the direction of arrow 254 either simultaneously or sequentially with the inner needle shaft 216. Alternatively, the outer needle shaft 224 may remain inserted at the tissue site, and subsequent inner needles may be inserted through the adaptor 270 and into the longitudinal passage of the outer needle 212 to obtain additional samples. In this situation, where the outer needle shaft 224 remains inserted at the tissue site, use of the adaptor 270 enables the operator to easily and safely insert the subsequent inner needles without getting caught within the hub 230 of the outer needle 212.

While this invention has been particularly shown and described with references to example embodiments thereof, it will be understood by those skilled in the art that various changes in form and details may be made therein without departing from the scope of the invention encompassed by the appended claims.

What is claimed is:

1. A method of sampling tissue, the method comprising:
   inserting an adaptor having a cylindrical body into a hub of an outer needle;
   inserting the outer needle into a patient and positioning the outer needle adjacent a site of tissue sampling;
   inserting a distal end of a first inner needle though a tapered longitudinal passage of the adaptor and into a longitudinal passage of the outer needle;
   extending the first inner needle through the longitudinal passage of the outer needle to position the distal end of the first inner needle adjacent the site of tissue sampling;
   moving the first inner needle in a reciprocating motion within the outer needle to cause the distal end of the first inner needle to aspirate tissue from the site of tissue sampling into a longitudinal passage of the first inner needle;
   removing the first inner needle from the site of tissue sampling and outer needle;
   inserting a distal end of a second inner needle though the tapered longitudinal passage of the adaptor and into the longitudinal passage of the outer needle;
   extending the second inner needle through the longitudinal passage of the outer needle to position the distal end of the second inner needle adjacent the site of tissue sampling; and
   moving the second inner needle in a reciprocating motion within the outer needle to cause the distal end of the second inner needle to aspirate additional tissue from the site of tissue sampling into a longitudinal passage of the second inner needle.

2. A method as in claim 1 wherein the cylindrical body of the adaptor includes a plastic core containing the tapered longitudinal passage, and an outer elastomeric layer to create a tight fit within the hub of the outer needle, and inserting the adaptor into the hub of the outer needle includes pressing the adaptor tightly into the hub of the outer needle.

3. A method as in claim 1 wherein the hub of the outer needle is a male luer fitting, the adaptor includes a female luer fitting, and inserting the adaptor into the hub of the outer needle includes screwing the female luer fitting of the adaptor onto the male luer fitting of the outer needle.

4. A method as in claim 1 wherein the site of tissue sampling is a thyroid gland or lymph node.

* * * * *